(12) United States Patent
De Vries et al.

(10) Patent No.: US 9,775,622 B2
(45) Date of Patent: Oct. 3, 2017

(54) BULKING AGENT APPLICATOR FOR TREATING FEMALE URINARY INCONTINENCE

(71) Applicant: Urogyn B.V., Nijmegen (NL)

(72) Inventors: Jan Albert De Vries, Zelhem (NL); Robert Jan Mrugas, Warsaw (PL)

(73) Assignee: UROGYN B.V., Nijmegen (NL)

( * ) Notice: Subject to any disclaimer, the term of this patent is extended or adjusted under 35 U.S.C. 154(b) by 142 days.

(21) Appl. No.: 14/396,306

(22) PCT Filed: Apr. 24, 2013

(86) PCT No.: PCT/EP2013/058486
§ 371 (c)(1),
(2) Date: Oct. 22, 2014

(87) PCT Pub. No.: WO2013/160347
PCT Pub. Date: Oct. 31, 2013

(65) Prior Publication Data
US 2015/0141742 A1 May 21, 2015

(30) Foreign Application Priority Data
Apr. 24, 2012 (EP) .................................. 12165391

(51) Int. Cl.
*A61B 17/12* (2006.01)
*A61B 17/34* (2006.01)
(Continued)

(52) U.S. Cl.
CPC ........ *A61B 17/12186* (2013.01); *A61B 1/018* (2013.01); *A61B 1/303* (2013.01);
(Continued)

(58) Field of Classification Search
CPC .......... A61B 17/12186; A61B 17/3403; A61B 17/3468; A61B 2017/3411;
(Continued)

(56) References Cited

U.S. PATENT DOCUMENTS 4,245,623 A    1/1981  Erb
5,385,561 A *  1/1995  Cerny ................ A61B 17/3417
                                              604/111

(Continued)

FOREIGN PATENT DOCUMENTS

GB    2343845 A    5/2000
NL    9301515      4/1995
(Continued)

OTHER PUBLICATIONS

International Search Report and Written Opinion mailed Jul. 11, 2013 for corresponding International Application No. PCT/EP2013/058486, filed Apr. 24, 2013.
(Continued)

*Primary Examiner* — Navin Natnithithadha
*Assistant Examiner* — Sunita Reddy
(74) *Attorney, Agent, or Firm* — Steven M. Koehler; Westman, Champlin & Koehler, P.A.

(57) ABSTRACT

Applicator for injecting a bulking agent at one or more selected submucosal positions in a periurethral tissue of a female patients' urethra. The applicator comprises a lance, such as a cystoscope with a distal end provided with one or more optical sensors, and a needle guide with a bore receiving the lance. The needle guide comprises needle channels at different angular positions, each needle channel extending between a needle entrance surface and an opposite shoulder surface. The needle channels are oriented to direct a needle via external peripheral tissue of the urethral meatus
(Continued)

to a submucosal position at a urethra section, e.g., within the optical scope of the optical sensor.

18 Claims, 4 Drawing Sheets

(51) Int. Cl.
*A61B 1/018* (2006.01)
*A61B 1/303* (2006.01)
*A61F 2/00* (2006.01)
*A61B 17/00* (2006.01)
*A61B 90/00* (2016.01)

(52) U.S. Cl.
CPC .... *A61B 17/12036* (2013.01); *A61B 17/3403* (2013.01); *A61B 17/3468* (2013.01); *A61B 17/3478* (2013.01); *A61F 2/0004* (2013.01); *A61B 90/361* (2016.02); *A61B 2017/00805* (2013.01); *A61B 2017/345* (2013.01); *A61B 2017/3407* (2013.01); *A61B 2017/3411* (2013.01)

(58) Field of Classification Search
CPC ........ A61B 2017/345; A61B 17/12036; A61B 90/361; A61B 2017/3407; A61B 17/3478; A61B 1/303; A61B 1/018; A61B 2017/00805; A61F 2/0004
USPC ............ 600/29–31; 128/897–899; 623/23.64
See application file for complete search history.

(56) References Cited

U.S. PATENT DOCUMENTS

| | | | |
|---|---|---|---|
| 5,749,894 A | 5/1998 | Engelson | |
| 6,015,424 A | 1/2000 | Rosenbluth et al. | |
| 6,024,754 A | 2/2000 | Engelson | |
| 6,053,860 A * | 4/2000 | Brooks | A61B 17/00491 600/104 |
| 6,071,230 A * | 6/2000 | Henalla | A61B 17/062 600/29 |
| 6,375,669 B1 | 4/2002 | Rosenbluth et al. | |
| 6,572,532 B1 * | 6/2003 | Pratt | A61B 1/00147 600/102 |
| 8,147,397 B1 * | 4/2012 | Witzmann | A61B 17/062 600/29 |
| 2003/0161824 A1 * | 8/2003 | Rackley | A61M 5/3286 424/125 |
| 2005/0187561 A1 | 8/2005 | Lee-Sepsick et al. | |
| 2006/0144406 A1 | 7/2006 | Nikolchev et al. | |
| 2007/0000496 A1 | 1/2007 | Nikolchev et al. | |
| 2007/0049790 A1 * | 3/2007 | Wagner | A61F 2/0045 600/37 |
| 2009/0277455 A1 | 11/2009 | Lee-Sepsick et al. | |
| 2012/0042879 A1 | 2/2012 | Lee-Sepsick et al. | |
| 2012/0130282 A1 * | 5/2012 | Galloway | A61M 25/0084 600/587 |
| 2013/0220334 A1 | 8/2013 | Lee-Sepsick et al. | |

FOREIGN PATENT DOCUMENTS

| | | | |
|---|---|---|---|
| NL | 9301515 A | | 4/1995 |
| WO | 9955239 | | 11/1999 |
| WO | WO0051676 | * | 9/2000 |
| WO | 2005082299 | | 9/2005 |
| WO | 2007137148 A2 | | 11/2007 |
| WO | 2011017306 A2 | | 2/2011 |

OTHER PUBLICATIONS

International Search Report and Written Opinion mailed Sep. 9, 2013 for International Application No. PCT/EP2013/058380, filed Apr. 23, 2013.

Chinese Office Action for corresponding Chinese patent application No. 201380030999.8, dated May 25, 2016.

* cited by examiner

BULKING AGENT APPLICATOR FOR TREATING FEMALE URINARY INCONTINENCE

CROSS-REFERENCE TO RELATED APPLICATION

This application is a Section 371 National Stage Application of International Application PCT/EP2013/058486 filed Apr. 24, 2013 and published as WO2013/160347 A1 in English.

BACKGROUND

The discussion below is merely provided for general background information and is not intended to be used as an aid in determining the scope of the claimed subject matter.

The present invention relates to an applicator for injecting a bulking agent at selected positions in a periurethral tissue for the treatment of female urinary incontinence. The invention also relates to a needle guide for such an applicator.

Urinary incontinence can result from a variety of causes, such as age, disease, pregnancy or trauma. Some patients particularly suffer from urinary incontinence during physical activities putting pressure on the bladder, such as sneezing, laughing, or lifting.

Urinary incontinence can be treated by submucosal injection of a bulking agent into the patients' periurethral tissue. WO 2007/137148 discloses a needle guide device used for positioning needles to inject a bulking agent at three or more positions into the urethral wall of a female patient.

SUMMARY

This Summary and the Abstract herein are provided to introduce a selection of concepts in a simplified form that are further described below in the Detailed Description. This Summary and the Abstract are not intended to identify key features or essential features of the claimed subject matter, nor are they intended to be used as an aid in determining the scope of the claimed subject matter. The claimed subject matter is not limited to implementations that solve any or all disadvantages noted in the background.

An aspect of the invention to provide a device for treating female urinary incontinence by injection of a bulking agent into the urethra wall allowing more accurate targeting of the needles to form a more uniform reinforcement of the local urethra wall. Preferably, the device should be low-cost.

An aspect of the invention is achieved with an applicator for injecting a bulking agent at selected submucosal positions in a periurethral tissue of a female patients' urethra, the applicator comprising a lance and a needle guide with a bore receiving the lance, the needle guide comprising needle channels extending between a needle entrance surface and an opposite shoulder surface, wherein the needle channels are positioned at angular distances from each other around a longitudinal axis of the lance.

This way, a needle can accurately be positioned at different angular positions around the urethra without the need to rotate the applicator or the needle guide for repositioning the needle. The bulking agent can accurately be applied at different sides of the urethra resulting in a more uniform reinforcement of the urethra wall. The needle channels are oriented to direct a needle through external peripheral tissue around the urethral meatus to a submucosal position at a urethra section. There is no need to apply a vacuum to move the targeted urethral wall in front of the needle channel. Injection takes place externally via peripheral tissue at the urethral meatus without piercing internal urethral tissue. The needle guide does not have a shoulder which needs to be inserted into the urethra but the shoulder surface can be positioned against the vulva.

In this respect, the angular distance between two positions refers to the angle between a line joining one of the positions to the longitudinal axis of the endoscopic lance and a line joining the other position to the longitudinal axis, in a plane perpendicular to the longitudinal axis, i.e., viewed in a direction coinciding with the longitudinal axis.

The lance can for example be an endoscopic lance comprising a distal end with one or more optical sensors. The endoscopic lance can for instance be a cystoscope or a sheath encasing a cystoscope. The needle guide can be mounted onto the endoscopic lance in such way that the bulking agent can be injected at a submucosal position of a urethral section within the optical scope or reach of the optical sensors. This allows accurate monitoring of the treated urethral section during injection. Alternatively, the lance can be a rod or bar for centering the applicator by insertion of the bar or rod into the patient's urethra.

Cystoscopes are typically used with a sheath encasing the actual cystoscope. Such a sheath typically comprises a number of lumens for encasing the cystoscope with its associated wiring and for channeling irrigation fluids, such as water or isotonic salt solutions. The needle guide can be coupled, for instance directly onto a cystoscope or onto a sheath encasing the cystoscope.

If the needle guide is positioned directly onto a cystoscope without the use of a sheath the needle guide can for instance be provided with an irrigation aperture connectable to a source of an irrigation fluid, for instance by means of a luer lock connection.

The cystoscope can be provided with a distal end with one or more optical sensors communicative with one or more remote viewing units. The cystoscope will typically also comprise a light source at the distal end. The distal end of the sheath is generally shaped to guide the optical scope of the cystoscope.

The needle channels of the needle guide are oriented to direct a needle to the respective targeted position, e.g., within the optical scope or reach of an optical sensor of an endoscopic lance, such as a cystoscope, via tissue peripheral to the urethral meatus. To this end, the needle channels may for instance comprise a channel exit at the shoulder surface of the needle guide, wherein the radial distance between each channel exit and the longitudinal axis of the endoscopic lance is at least 8 mm, e.g., at least 11 mm.

In a specific embodiment, the needle guide comprises a slot giving access to the bore receiving the lance. This way, the needle guide can be clicked onto the lance at a desired position. Other click-on attachments can also be used. To allow accurate positioning of the needle guide, the bore may be dimensioned to receive the endoscopic lance in a slideable manner and the needle guide may be provided with a clamp or fastener fixating the needle guide when it is in the desired position on the endoscopic lance.

The needle guide can be positioned on the lance in such a way that the injection areas are about halfway the sphincter and the urethral meatus. Hence, the preferred position of the needle guide on the lance depends on the length of the patients' urethra. In case of a long urethra the distance between the needle guide and the distal end of the lance can for example be about 2.5-3.5 cm, e.g., about 3 cm. In case of an average length urethra the distance between the needle guide and the distal end of the lance can for example be about 1.5-2.5 cm, e.g., about 2 cm. In case of a short urethra the distance between the needle guide and the distal end of the lance can for example be about 0.8-1.5 cm, e.g., about 1 cm.

In a specific embodiment the needle guide may comprise an array of needle channels, e.g., of three, four or more needle channels, the array being centered about the longitudinal axis of the lance. The needle channels may be arranged at essentially equidistant angular positions relative to the longitudinal axis of the lance when the needle guide is coupled to the lance. Considering the adjacent anatomy with an average female patient, in particular the presence of the vagina, it is practically advantageous to apply three injections at substantially the same axial and radial distance spaced by angular distances of about 120 degrees, e.g., at a 2 o'clock, 6 o'clock and 10 o'clock position (the 6 o'clock direction being the direction towards the vagina). To this end the needle guide may be provided with three needle channels at an angular distance of 120 degrees from each other. Alternatively, four or more injections can be applied at substantially the same axial and radial distance. For instance, four positions can be positioned at regular angular distances of about 90 degrees, or optionally with a slight shift towards the 6 o'clock position: for instance at a 2 o'clock, 5 o'clock, 7 o'clock and 10 o'clock position, respectively. In that case, the needle guide may be provided with four needle channels at corresponding angular distances from each other, e.g., at angular distances of about 90 degrees, or at distances of 120, 90, 60 and 90 degrees, successively.

The aforementioned angular distances are relative to the longitudinal axis of the needle guide. The bore of the needle guide is configured to receive the lance in such a way that the longitudinal axis substantially coincides with the axis of the needle guide. Cystoscopes are typically substantially cylindrical. Sheaths encasing a cystoscope are available in various shapes and sizes. If a needle guide is used for use on a sheath, the bore should be configured in such a way that the axis of the central bore of the needle guide substantially coincides with the longitudinal axis of the sheath.

The needle channels can be oriented to be directed in use to a submucosal position of a periurethral wall, preferably within the optical scope of the optical sensor. The needle channels may converge towards the targeted position by making an angle of about 0-10 degrees, e.g., of about 2-7 degrees, such as about 4-6 degrees, in particular about 5 degrees with the longitudinal axis of the lance.

The needle channels may for instance have a substantially cylindrical inner surface dimensioned to receive a needle with a clearance fit. To allow easier access of a needle, the channels may be narrowing down conically in the direction of needle insertion or they may have a narrowing entrance section.

The targeted positions of the urethra wall can for instance be at least 2 mm from the lance in the distal end of the applicator. To enable good monitoring of the injections the targeted positions of the urethra wall should preferably be at most 20 mm from the distal end of the applicator. The targeted positions of the urethra wall can for instance be at 6-15 mm from the distal end of the applicator. A suitable distance is for instance about 10+/−2 mm from the distal end of the applicator.

The injections are submucosal, e.g. at a radial distance of about 4-8 mm from the inner urethral surface, or about 5-9, e.g. about 7 mm+/−0.6 mm from a central axis of the urethra.

The main shape of the needle guide—apart from recesses such as a click-on slot receiving the cystoscope—can for example be cylindrical or frusto-conical, having a longitudinal axis which coincides with the longitudinal axis of the lance after placement of the needle guide on the lance.

The needle guide comprises a shoulder surface for abutting the urethral meatus during treatment of the patient. For ergonomic compliance with local anatomy of an anthropometrically average patient, the needle guide may have a substantially circular or oval shoulder surface with a maximum diameter of about 25-30 mm, e.g., about 28 mm+/−1 mm.

The bulking agent may for instance be injected at a distance from the sphincter, typically about halfway between the sphincter and the urethral meatus in the mid-urethral section. The length of the urethra will vary with each patient. As a consequence, the optimal positions where the bulking agent could be injected—and accordingly the desired distance between the needle guide and the distal end of the lance—may vary per case. To allow accurate positioning for any urethral length a set of interchangeable needle guides can be used with different axial lengths. In this respect the axial length is the length of the needle guide in the longitudinal direction of the cystoscope when the needle guide is coupled to the lance.

Such a set of needle guides may for example comprise:

a first needle guide for positioning on a lance, such as a cystoscope or sheath, at an axial distance from the distal end of the lance corresponding to the axial distance between the distal end of the lance and a targeted periurethral tissue;

a second needle guide for positioning at twice said axial distance; and a third needle guide for positioning at about three times said axial distance.

Optionally the set of needle guides may include further needle guides of different sizes.

The set may for example comprise needle guides of different axial lengths having the same configuration of needle channels, e.g. having a same converging angle and showing the same angular distances between the needle channels. Optionally, the needle guides may have the same needle entrance surfaces.

Optionally a color code can be used to distinguish between available sizes.

Suitable bulking agents include, but are not limited to, beads, particles, and swellable or non-swellable polymers or oligomers, such as a curable elastomer compounds, such as a two-component polysiloxane, such as poly dimethyl siloxane, optionally with blocked hydroxyl groups. Other bulking agents can also be used if so desired.

The needle can for instance be a hypodermic needle of a syringe. The syringe typically comprises a shaft for pushing a plunger with aid of a thumb pad and, e.g., barrel ears. Any syringe capable of forcing the bulking agent down its needle may suffice. A suitable syringe may for instance have a capacity of about 1 ml and a length of about 4-6 centimeters long. Suitable needle sizes can for example be about 16-20 gauge. Some embodiments have a capacity of between about 1-3 ml. In one embodiment, the syringe has a capacity of at least about 1 ml, a needle size of about 18 gauge, and a needle length of at least about 5 cm.

To position the needle guide onto the lance, such as a cystoscope or its sheath, a positioner can be used, with a longitudinal bore for receiving the lance, wherein the length of the positioner and the bore correspond to the desired distance between the needle guide and the distal end of the applicator. After coupling the needle guide with the lance in a slideable manner, the distal end of the cystoscope can be inserted into the bore of the positioner until one end face of the positioner is at the position of the distal end of the lance. The needle guide can then be moved to abut the opposite end face of the positioner. Subsequently, the needle guide can be fixated and the positioner can be removed. The positioner can for instance be a transparent block. The positioner can for instance have a contact face for engaging the needle guide, wherein the contact face is profiled to match the contour of the shoulder surface of the needle guide.

When the needle guide is fixated to the lance at the right position, the positioner, if used, can be removed and the lance can be inserted into the urethra of the female patient until the needle guide abuts the urethral meatus between the labia minora. The periurethral wall will snugly fit around the lance. The needle guide can be positioned such that a needle channel is or can be directed towards each targeted injection area of the periurethral wall. A number of, e.g., an array of three or four injection areas can be used, although less or more areas can also be used if so desired. The applicator can be rotated until the positions of the needle channels are in line with the targeted injection areas.

A syringe with a needle is filled with an appropriate amount of an injectable bulking agent. The needle of the syringe is then inserted into one of the needle channels until the reservoir of the syringe abuts the needle guide. At this point the terminal end of the needle should have reached the targeted injection area and the contents of the syringe can be injected. As a result of the injection the treated periurethral wall section will bulge. If the surface of the targeted periurethral wall section is within the scope or observation range of the cystoscope the bulging by the periurethral tissue can be monitored during the injections. If the bulge appears to be sufficiently large the injection can be stopped and the needle can be withdrawn. A next needle can then be positioned into a next needle channel of the needle guide to inject a next targeted injection area.

The invention also relates to a method for treating female urinary incontinence by injecting bulking material at selected periurethal positions using an applicator with a lance and a needle guide with a bore receiving the lance, and needle channels around the bore, the method comprising the steps of:

inserting the lance into a urethra until needle guide abuts the urethra meatus, inserting a needle of an injector through a first one of the needle channels and moving a tip of the needle through external tissue around the urethra meatus to a first selected periurethral position;

injecting the bulking agent at the first periurethral position via the needle while the needle is in said first needle channel;

maintaining the needle guide at the same position, while removing the needle from the first needle channel and inserting the needle into a second one of the needle channels and moving a tip of the needle through external tissue around the urethra meatus to a second selected periurethral position;

injecting the bulking agent at the second periurethral position via the needle while the needle is in said second needle channel;

optionally repeating the two preceding steps for injecting the bulking agent at one or more subsequent periurethral positions.

Optionally, the lance is an endoscopic lance such as a cystoscope. The needle guide can be positioned on the lance in such a way that the periurethral positions where the bulking agent is injected, are within an observation range or scope of the endoscopic lance.

BRIEF DESCRIPTION OF THE DRAWINGS

Aspects of the invention will be further explained under reference to the accompanying drawings, in which.

DETAILED DESCRIPTION OF THE ILLUSTRATIVE EMBODIMENTS

Figure 1:
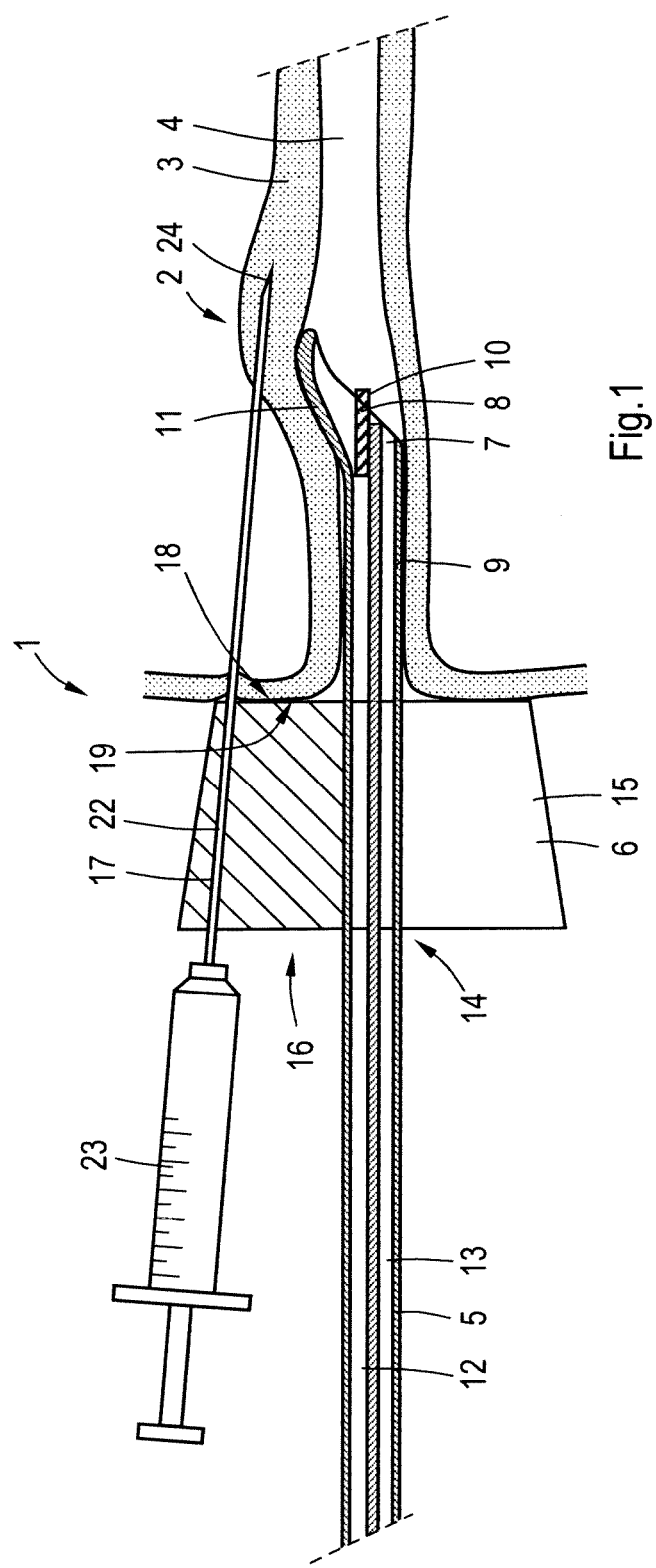
FIG. 1 shows schematically in longitudinal cross section a first exemplary embodiment of an applicator.

FIG. 1 shows an applicator 1 for injecting a bulking agent at selected positions 2 in the periurethral tissue 3 of a female patients' urethra 4 for the treatment of stress induced urinary incontinence. The applicator 1 comprises an endoscopic lance 5 and a needle guide 6 clicked onto the endoscopic lance 5. In FIG. 1 a distal end 7 of the endoscopic lance 5 is inserted into the urethra 4.

The endoscopic lance 5 comprises a cystoscope 8 and a sheath 9 encasing the cystoscope 8. The distal end 7 of the cystoscope 8 is provided with an optical sensor 10. The distal end of the sheath 9 is provided with an asymmetrically offset nose 11 locally widening the urethra 4 to improve the optical scope of the sensor 10. The sheath 9 comprises a lumen 12 encasing the cystoscope 8 and one or more further lumens 13, e.g., for the transport of processing liquids such as flushing water, e.g., for flushing the optical sensor 10 when contacting the urethral mucosa blurs the optical sensors' imaging.

The needle guide 6 comprises a frusto-conical body 15 with a central bore 14 extending in axial direction, and a radially extending slot 16 giving radial access to the bore 14. The bore 14 is dimensioned to receive the sheath 9 in a slideable manner in such a way that the central axis of the bore 14 substantially coincides with the longitudinal axis of the cystoscope 8 encased in the sheath 9. The slot 16 has a width which is less than the diameter of the bore 14 but which is sufficient to allow easy passage of the sheath 9. This way, the needle guide 6 can be clicked onto the sheath 9. The needle guide 6 can subsequently be clamped in the right position on the sheath 9 by means of a fastener (not shown).

Figure 2A:
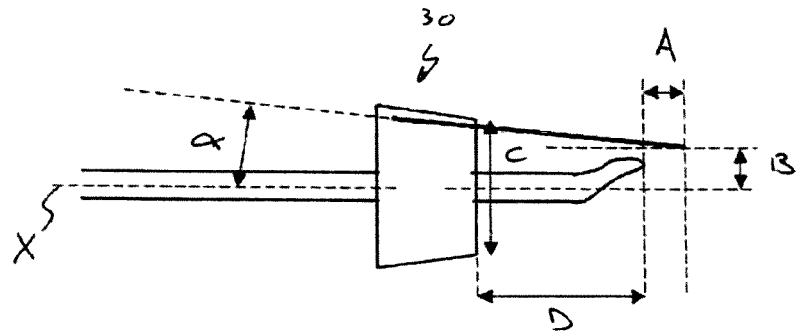
FIG. 2A-C schematically show a set of three needle guides of different size.
Figure 2B:
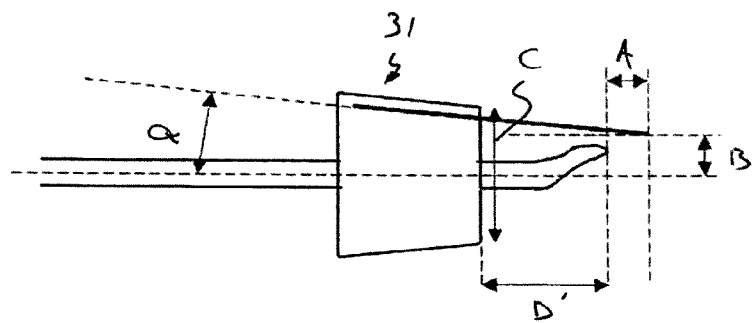
Figure 2C:
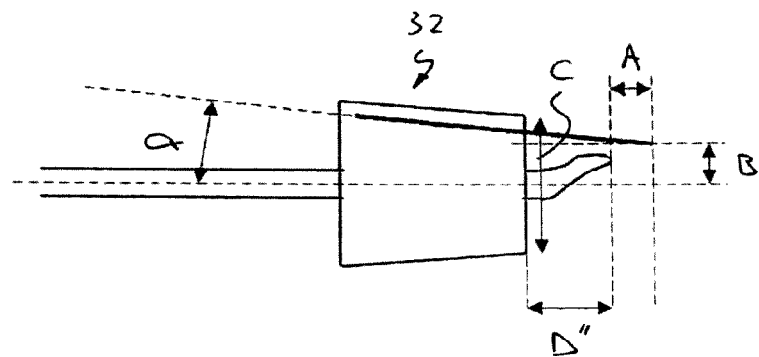

The needle guide 6 comprises a number of needle channels 17 which, in use, are directed to the selected submucosal positions 2 of the periurethral wall section within the optical scope of the optical sensor 10. As illustrated in FIGS. 2A-C the targeted submucosal position 2 is at a distance A, typically of about 8-12 mm, in front of the distal end 7 of the sheath 9 and at a radial distance B of about 6-8 mm from the longitudinal central axis of the cystoscope 8.

In the exemplary embodiment of FIG. 1, the needle guide 6 comprises a circular shoulder surface 18 with a diameter of about 28 mm to abut the patients' urethral meatus 19. The needle channel 17 makes an angle of about 5 degrees with the central axis X of the cystoscope 8.

A needle 22 of a syringe 23 containing a biocompatible bulking agent is inserted into one of the needle channels 17 to penetrate peripheral tissue on its way to the targeted injection area 2. After the needle point 24 reaches the targeted area 2 content of the syringe 23 is injected, resulting in gradual bulging of the injected periurethral section 2. This bulging is monitored via the cystoscope 8. When the injected periurethral section 2 has sufficiently bulged, injection can be stopped and the needle 22 can be withdrawn. The needle 22, or a needle of a next syringe, can then be inserted into a next needle channel 17 until all selected injection areas have been treated.

FIGS. 2A-C show respective needle guides 30, 31, 32 of a set of differently sized needle guides. The set of needle guides 31-32 comprises a first needle 30 guide shown in FIG. 2A which is configured to be positioned at an axial distance D from the distal end 7 of the cystoscope 8 corresponding to about three times the axial distance A between the distal end 7 of the cystoscope 8 and the respective targeted periurethral position 2. This axial distance A between the distal cystoscope end and the targeted tissue is for instance about 10 mm+/−2 mm. In that case the distance D between the shoulder surface 18 of the needle guide 6 and the distal cystoscope end 7 is about 30 mm. This needle guide 6 is particularly useful for patients with a relatively long urethra.

The set further comprises a second needle guide 31 shown in FIG. 2B which is configured to be positioned at an axial distance D' from the distal end 7 of the cystoscope 8 corresponding to about twice the axial distance A between the distal end 7 of the cystoscope 8 and the targeted periurethral position 2, e.g., about 20 mm. This needle guide 31 is particularly useful for patients with a urethra of an average length.

A third needle guide 32 of the set is shown in FIG. 2C and is particularly useful for patients with a relatively short urethra. This needle guide 32 is configured to be positioned at about the same distance D" as the axial distance A between the distal end 7 of the cystoscope 8 and the targeted periurethral position 2.

Figure 3:
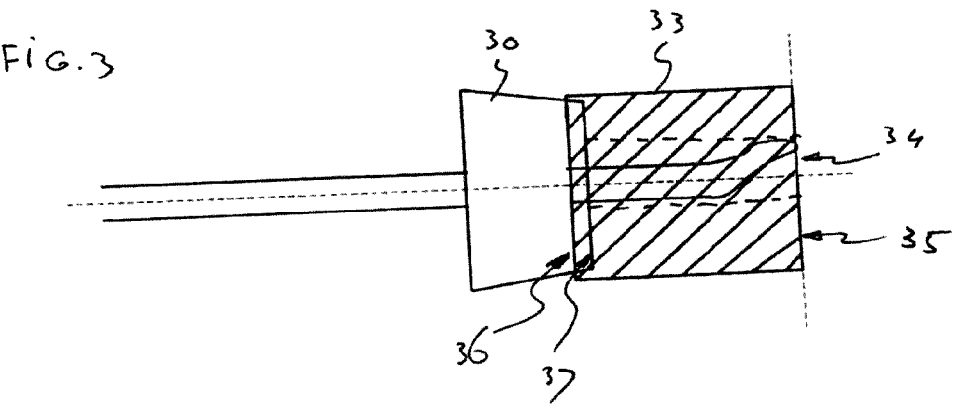
FIG. 3 shows schematically a positioner used for positioning a needle guide.

A positioner 33 can be used for accurately positioning the needle guide on the cystoscope sheath 9, as is shown in FIG. 3. The positioner 33 is a cylindrical block of a transparent material with a longitudinal bore 34 for receiving the sheath 9. The axial length of the positioner 33 and the bore 34 correspond to the desired distance between the needle guide 6 and the distal end 7 of the sheath 9. After coupling the needle guide 6 with the cystoscope 8 in a slideable manner, the distal end 7 of the cystoscope 8 is inserted into the bore 34 of the positioner 33 until the distal end face 35 of the positioner 33 is at the position of the distal end 7 of the cystoscope 8, as shown in FIG. 3. The needle guide 6 can then be moved to abut the opposite end face 36 of the positioner 33. This end face 36 comprises a cylindrical recess 37 matching the contour of the shoulder surface 18 of the needle guide 6. Finally, the needle guide 6 is clamped onto the sheath 9 to fixate its position and the positioner 33 is removed.

Figure 4A:
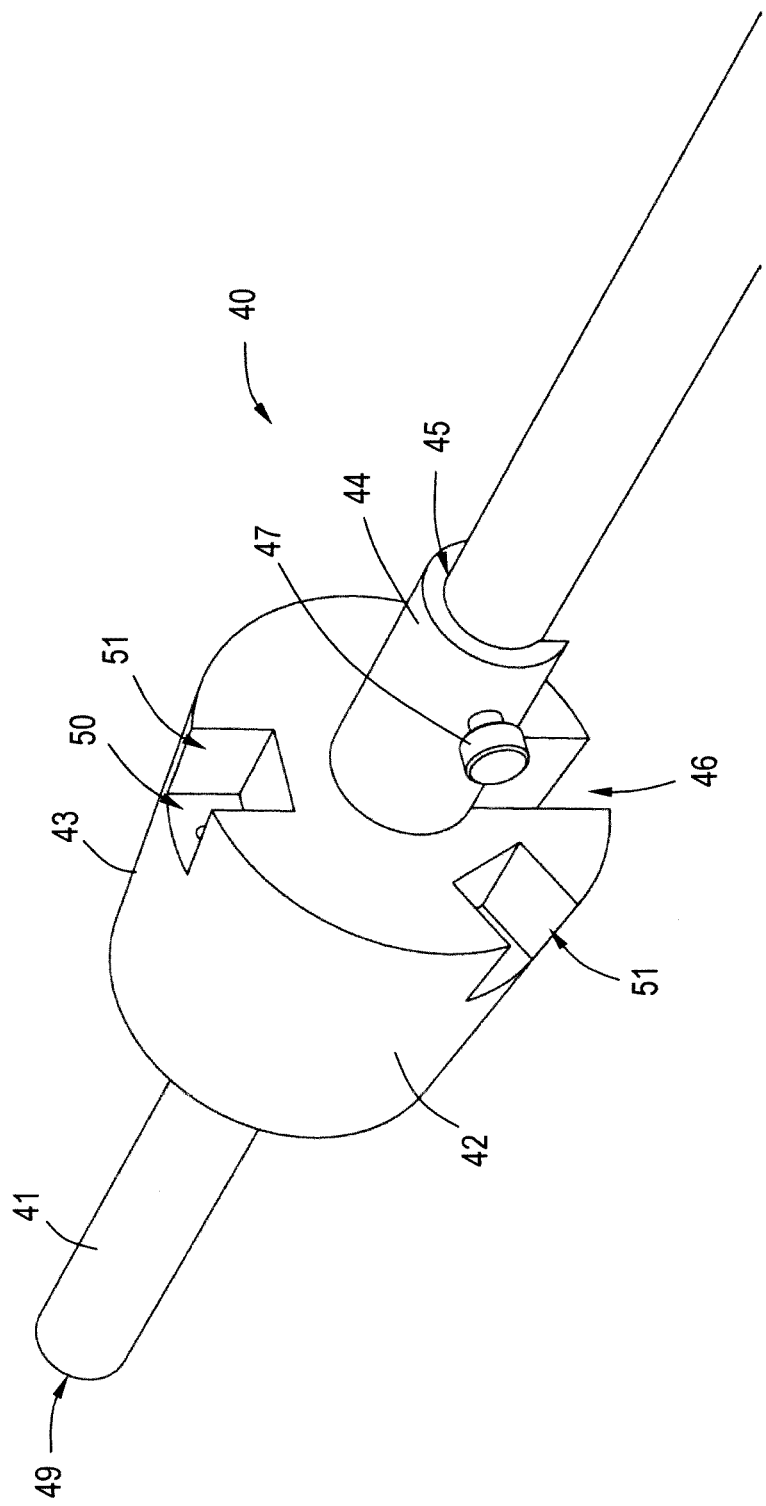
FIG. 4A shows in perspective view a second exemplary embodiment of the applicator.
Figure 4C:
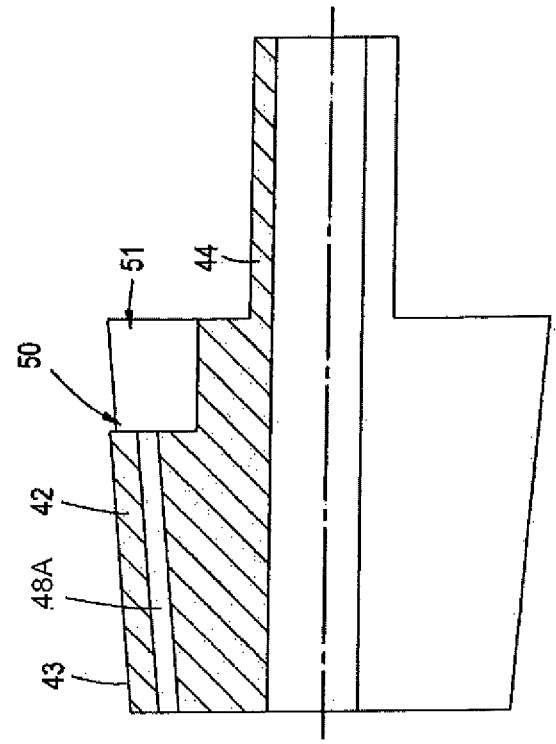
FIG. 4C shows the applicator of FIG. 4A in axial cross section.
Figure 4B:
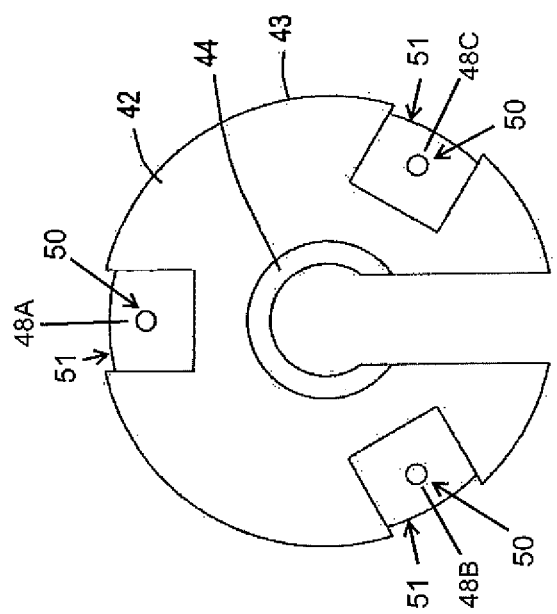
FIG. 4B shows in rear view the applicator of FIG. 4A.

FIGS. 4A-C show an alternative embodiment of an applicator 40. The applicator 40 comprises a cystoscope 41 and a needle guide 42 directly attached onto the cystoscope 41 without the presence of a sheath encasing the cystoscope 41. The needle guide 42 comprises a frusto-conical body 43 and an extension 44 pointing away from the distal end 49 of the cystoscope 41. This extension 44 has a substantially U-shaped cross section in line with a central bore 45 in the frusto-conical body 43 for receiving the cystoscope 41 in a slideable manner, in such a way that the longitudinal axis of the cystoscope substantially coincides with the central axis of the bore 45. The frusto-conical body 43 comprises a radial slot 46, slightly narrower than the bore diameter. The radial slot 46 gives access to the central bore 45 and allows lateral insertion of the cystoscope 41. After insertion of the cystoscope 41 the needle guide 42 can be moved to the desired position onto the cystoscope 41 and be fixated by fastening a screw 47 for clamping the extension 44 onto the cystoscope 41. As with the embodiment of FIG. 1, the needle guide 42 comprises an array of three equidistantly arranged needle channels 48 (identified in FIG. 4B as channels 48A, 48B, and 48) each converging towards the distal end 49 of the cystoscope 41 under an angle of about 5 degrees. The needle channels 48A, 48B, and 48C each comprise an entrance 50 positioned in a radially extending recess 51 at the side of the needle guide 42 where the needles are inserted.

The invention claimed is:

1. An applicator for injecting a bulking agent at one or more selected submucosal positions in a periurethral tissue of a female patient's urethra, the applicator comprising:
   a lance; and
   a needle guide comprising:
   a needle entrance surface and an opposite shoulder surface;
   a bore receiving the lance; and
   an array of needle channels extending between the needle entrance surface and the opposite shoulder surface, wherein the needle channels are oriented to direct a needle through external peripheral tissue around a urethral meatus to a submucosal position at a urethra section, and wherein the needle channels of the array are arranged concurrently at different radial positions with respect to a circumference of the needle guide around a longitudinal axis of the lance.

2. The applicator according to claim 1, wherein the lance is an endoscopic lance comprising a distal end with one or more optical sensors.

3. The applicator according to claim 1, wherein a radial distance between each needle channel of the needle channels and the longitudinal axis of the lance at the opposite shoulder surface is between at least 5 mm from the longitudinal axis of the lance and less than a radial distance of an external edge of the needle guide.

4. The applicator according to claim 1, wherein the needle channels are oriented to direct a needle to a position at an axial distance of 5-20 mm from a distal end of the lance.

5. The applicator according to claim 1, wherein the needle channels converge in a direction of a distal end of the lance by making an angle of greater than 0 degrees and equal to or less than 10 degrees with the longitudinal axis of the lance.

6. The applicator according to claim 1, wherein the lance comprises a cystoscope.

7. The applicator according to claim 6, wherein the needle guide is coupled to the cystoscope or to a sheath encasing the cystoscope by a click-on attachment.

8. The applicator according to claim 7, wherein the bore of the needle guide receives the cystoscope or a sheath encasing the cystoscope in a slideable manner, wherein the cystoscope or the sheath are encased in the bore, wherein a central axis of the bore coincides with the longitudinal axis of the lance, and wherein the needle guide comprises a fastener for fixating the needle guide on a desired position on the cystoscope or the sheath.

9. The applicator according to claim 1 wherein the opposite shoulder surface of the needle guide has a diameter between a diameter of the bore and 35 mm.

10. The applicator according to claim 1 wherein the needle guide comprises three or four equidistantly arranged needle channels centered about the longitudinal axis of the lance.

11. The needle guide according to claim 1, wherein each needle channel is at substantially the same radial distance from the longitudinal axis of the lance.

12. The needle guide according to claim 1, wherein the needle channels are oriented to positions at a same axial position along the longitudinal axis of the lance.

13. The needle guide according to claim 1, wherein the radial distances between each needle channel of the needle channels and the longitudinal axis of the lance are equal.

14. The needle guide according to claim 1, wherein the needle channels are oriented to positions at a same axial position along the longitudinal axis, and wherein the radial distances between each needle channel of the needle channels and the longitudinal axis of the lance are equal.

15. An apparatus comprising a needle guide configured to receive a lance configured to inject a bulking agent at one or more selected submucosal positions in a periurethral tissue of a female patient's urethra, the lance having a longitudinal axis, the needle guide comprising:
 a needle entrance surface and an opposite shoulder surface;
 a bore extending between the needle entrance surface and the opposite shoulder surface, the bore configured to receive the lance; and
 an array of needle channels separate from the bore and extending between the needle entrance surface and the opposite shoulder surface, wherein the needle channels of the array are concurrently separated from each other by radial angles with respect to a circumference of the needle guide around a longitudinal axis of the lance.

16. The apparatus according to claim 15 and further comprising a second needle guide to form a set of needle guides, the second needle guide comprising:
 a second needle entrance surface and a second opposite shoulder surface;
 a second bore configured to receive the lance; and
 second needle channels extending over a length of a longitudinal axis of the second needle guide, wherein the second needle channels are positioned at angular distances from each other relative to the longitudinal axis of the lance, wherein the length of the longitudinal axis of the second needle guide has a different axial length than a length of a longitudinal axis of the needle guide.

17. The apparatus according to claim 16, wherein the needle guide is configured to be positioned at an axial distance from a distal end of the lance, which axial distance corresponds to an axial distance between the distal end of the lance and the periurethral tissue; wherein the second needle guide is configured to be positioned at twice said axial distance; and further comprising a third needle guide configured to be positioned at three times said axial distance.

18. The apparatus according to claim 16, wherein the needle guide and the second needle guide have the same number of needle channels.

* * * * *